(12) United States Patent
Nguyen et al.

(10) Patent No.: US 7,488,470 B2
(45) Date of Patent: Feb. 10, 2009

(54) PROCESS FOR THE PERMANENT DEFORMATION OF KERATINOUS SUBSTANCES EMPLOYING AN ORGANIC ABSORBING AGENT

(75) Inventors: Ly-Lan Nguyen, L'Hay les Roses (FR); Anne Sabbagh, Rueil Malmaison (FR); Priscilla Devin-Baudoin, Sevres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/953,434

(22) Filed: Sep. 17, 2001

(65) Prior Publication Data

US 2002/0127194 A1    Sep. 12, 2002

(30) Foreign Application Priority Data

Sep. 18, 2000 (FR) .................................. 00 11890

(51) Int. Cl.
*A61K 8/00* (2006.01)
*A45D 7/04* (2006.01)
*A61K 8/02* (2006.01)

(52) U.S. Cl. .................... 424/70.2; 424/70.1; 424/70.4; 424/70.16; 424/401; 132/203; 132/204

(58) Field of Classification Search ................ 424/70.2, 424/70.4, 70.5, 70.51, 70.16; 132/203, 204
See application file for complete search history.

(56) References Cited

U.S. PATENT DOCUMENTS

| | | | | | |
|---|---|---|---|---|---|
| 3,399,683 | A | * | 9/1968 | Forbriger et al. | ................ 132/7 |
| 3,837,349 | A | * | 9/1974 | Jedzinak et al. | ................ 424/71 |
| 4,784,848 | A | * | 11/1988 | Koyama | ....................... 424/71 |
| 5,531,987 | A | | 7/1996 | Bauer et al. | ............... 424/76.21 |
| 6,344,183 | B2 | * | 2/2002 | Paul et al. | ....................... 424/47 |
| 6,365,140 | B1 | * | 4/2002 | Melby et al. | ................ 424/70.1 |
| 6,479,042 | B1 | * | 11/2002 | Nguyen et al. | .............. 424/70.5 |

FOREIGN PATENT DOCUMENTS

| | | |
|---|---|---|
| DE | 28 22 125 | 11/1979 |
| EP | 0 968 703 | 1/2000 |
| JP | 5017322 | * 1/1993 |
| WO | WO 99/18922 | 4/1999 |

* cited by examiner

*Primary Examiner*—Lakshmi S Channavajjala
(74) *Attorney, Agent, or Firm*—Steptoe & Johnson LLP

(57) ABSTRACT

A two-stage treatment process suitable for the permanent deformation and/or shaping of keratinous substances and, in particular, the hair includes the application of a reducing composition containing, in addition to a reducing agent, an organic absorbing agent followed, after an optional rinsing, by the application of a neutralizing composition and by the rinsing of the keratinous substances thus treated.

14 Claims, No Drawings

PROCESS FOR THE PERMANENT DEFORMATION OF KERATINOUS SUBSTANCES EMPLOYING AN ORGANIC ABSORBING AGENT

The present invention is directed to a novel process for the treatment of keratinous substances, in particular the hair, to produce permanent deformation of the latter. It is also targeted to a ready-for-use composition intended for this type of treatment of keratinous substances and to a kit comprising, in separate compartments, the various compositions necessary for this type of treatment.

As far as permanent deformation of the hair is concerned, it is known, in a first step, on hair which has been placed under tension beforehand (using rollers, curlers or other devices), to open the disulphide bonds of the cystine of the keratin using a composition comprising a reducing agent and then, generally after rinsing the hair, to reconstitute the disulphide bonds by applying a composition, generally an oxidizing composition, which makes it possible to fix the hairstyle. This technique thus makes it possible, without distinction, to wave or straighten or crimp the hair.

Reducing compositions for the permanent deformation of the hair generally comprise active principles which sensitize or irritate the skin. These compositions are often liquid. Inevitably, once a product is applied to hair wound around curlers and other devices, it flows onto the scalp, promoting cutaneous irritation.

In order to overcome this problem, attempts have been made to thicken the reducing composition. Nevertheless, for the active principles to act from the root to the end of the hair, the thickened product has to be applied before the hair is wound around the curlers. The leave-in time is highly variable from one lock to another and the results are not satisfactory.

Furthermore, hair is very often more sensitized at the ends than at the roots. The active principles of the reducing composition thus penetrate more readily at the end of the individual hair and the curling is consequently tighter at the end than at the root. One solution for overcoming this problem consists in applying, to the sensitized parts, a protective fluid which limits the penetration of the active principles. However, this solution is unsatisfactory insofar as it is difficult to precisely localize the application of the fluid. In addition, there is a risk of rendering the hair too slippery and thus of making the tensioning difficult.

Thiols are very generally used as reducing agents in reducing compositions. These thiol-comprising reducing agents have an unpleasant smell. Fragrances have been incorporated in reducing lotions in order to relatively effectively conceal this smell. Nevertheless, it is essential to place a cap over the hair during the leave-in time in order to limit the diffusion of the smell. When this cap is removed, a concentrated smell of thiol is given off by the hair and, in particular, by reduced hair, which smell is difficult to mask.

Thus, it is necessary to improve the techniques for the permanent deformation of the hair, in particular by overcoming the above problems.

More specifically, there exists a need for a novel process which makes it possible to carry out a permanent deformation of the hair which is devoid of the disadvantages expressed above and which, in particular, provides the hair with uniform deformations, curls or ringlets while acceptably limiting the risks of cutaneous sensitization and irritation and the unpleasant smell given off during the leave-in period.

Surprisingly and unexpectedly, the inventors have discovered that it is possible to solve the problems described above by using, in particular, in a process for the permanent deformation of the hair, a ready-for-use reducing composition comprising an organic agent with a precise absorption property.

The invention is thus directed to a novel process for the treatment of keratinous substances and, in particular, for the permanent deformation of the hair, comprising, in a first step, the application of a ready-for-use reducing composition comprising at least one organic absorbing agent and then, after a leave-in time necessary for the reduction of the keratinous substances, the application of a neutralizing composition, generally an oxidizing neutralizing composition.

The invention also relates to an extemporaneous reducing composition comprising at least one reducing agent and one organic absorbing agent.

The invention further relates to a first kit comprising, in a first compartment a reducing liquid comprising at least one reducing agent, in a second compartment a neutralizing composition and, in a third compartment an organic absorbing agent.

The invention still further relates to a second kit comprising, in a first compartment, a reducing liquid comprising at least one reducing agent and at least one organic absorbing agent and, in a second compartment, a neutralizing composition.

According to the present invention, a novel treatment process suitable for the permanent deformation and/or shaping of keratinous substances and in particular the hair is provided, characterized in that it comprises the following stages:

(i) in a first step, a reducing composition (a) combining at least one reducing agent and at least one organic absorbing agent is applied to the keratinous substance to be treated;

(ii) after a leave-in time necessary for the reduction of the keratinous substance, a neutralizing composition (b) is applied; and (iii) after a leave-in time necessary for the neutralization, the keratinous substance thus treated is rinsed.

The keratinous substance can be placed under tension, in particular, using rollers, curlers or similar devices, before, during or after the application of the reducing composition (a) of step (i).

The term "absorbing agent" is understood to mean any compound capable of rapidly trapping a large amount of water. The organic absorbing agent is therefore generally a hydrophilic or amphiphilic compound.

The term "absorbing agents" is understood to mean, within the meaning of the present invention, any compound having a static water absorption capacity at ambient temperature (25° C.) of greater than or equal to three times its weight.

The absorbing agents are preferably chosen from compounds having a static water absorption capacity of greater than or equal to five times their weight, and preferably greater than or equal to ten times their weight.

The test for measuring the static water absorption capacity consists, at ambient temperature, in evenly arranging the compound to be tested, in an amount of 1 gram, at the bottom of a 150 ml beaker with a diameter of approximately 6 cm; in adding water to the powder in an amount of 3 grams; and in leaving the mixture to stand for 1 minute without stirring. If no more free water, that is to say no more supernatant water, remains after the minute, the compound can be regarded as an absorbing agent within the meaning of the invention.

The process of the invention is particularly well suited to permed hair.

Applied to healthy hair, and even repeated several times, the process of the invention exhibits as main advantages, inter alia, beautiful and uniform curls or ringlets with a reduced release of unpleasant smells, on the one hand, and without irritation to the skin and to the scalp, on the other hand.

Other characteristics, aspects and advantages of the invention will become even more clearly apparent on reading the detailed description which follows and the concrete non-limiting example which illustrates the invention.

Although the description which follows refers essentially to the specific case of the treatment of hair, the process of the invention is applicable to any keratinous substance in general, in particular, eyelashes, moustaches, body hairs, wool and others.

The first stage of the process of the invention consists of the application of a reducing composition (a), before, during or after placing the hair under tension (by means of curlers, rollers or other devices).

The ready-for-use reducing composition (a) can be obtained by an extemporaneous mixing, at the time of use, of a reducing liquid comprising at least one reducing agent and of at least one organic absorbing agent.

The composition thus obtained can optionally be left to stand for at least one minute before use.

The absorbing agent can in particular be chosen from, alone or as a mixture, (1) crosslinked sodium carboxymethylcelluloses.

Such products are sold in particular by Avebe under the name Primellose.

(2) Wood sawdusts and flours with a mean particle size of less than 250 microns and in particular spruce flour or beech flour.

Such products are sold in particular by Parisienne des Sciures under the name T140 (spruce flour) or H160/0 (beech flour).

(3) Modified starches.

Natural starches generally do not have a good static water absorption capacity; it is generally necessary to modify them so as to obtain an absorbing agent within the meaning of the invention. Such a modification can consist of a grafting of weakly crosslinked sodium salts and/or of a pregelatinization.

Mention may be made, among the modified starches which can be used, of quaternized pregelatinized potato flours, pregelatinized maize starches, crosslinked potato carboxymethylstarches, pregelatinized and optionally hydroxypropylated manioc distarch phosphates or pregelatinized and optionally acetylated potato distarch phosphates.

Mention may be made, among commercially available products, of the products sold by Avebe under the names Pregel or Primogel or those sold by National Starch under the name Structure Zea.

(4) Certain polyacrylates and in particular those sold by Ozaka Yuki under the name PQ Polymer.

The absorbing agents which are particularly preferred are chosen especially from carboxymethylstarches.

Carboxymethylstarches can be provided in particular in the powder form or in the form of a suspension in a hydrophobic oil. The term "hydrophobic oil" is understood to mean, for example, cosmetically acceptable oils: mineral oils, fatty acid esters, vegetable oils, animal oils or synthetic oils.

The concentration of organic absorbing agents in the reducing composition (a) is between 0.1 and 25%, and preferably between 7 and 11%, by weight with respect to the total weight of the composition.

The reducing composition (a) comprises between 0.5 and 20%, preferably 4 to 15%, by weight of reducing agent with respect to the total weight of the composition.

The reducing composition (a) preferably comprises at least one thiol-comprising reducing agent chosen from thiogly-colic acid or its salts, thiolactic acid or its salts, cysteine, cysteamine and glycerol thioglycolate.

The pH of the reducing composition (a) is between 5 and 11, preferably between 6 and 10, and more preferably still between 8.5 and 9.5.

In addition, the reducing composition (a) advantageously comprises at least one alkaline agent which can be chosen in particular from ammonia, monoethanolamine, diethanolamine, triethanolamine, isopropanolamine, 1,3-propanediamine, an alkali metal or alkaline earth metal or ammonium carbonate or bicarbonate, an organic carbonate, such as guanidine carbonate, or an alkali metal or alkaline earth metal hydroxide, used alone or as a mixture.

According to a particularly advantageous aspect of the process according to the invention, the reducing composition (a) is applied to wet hair. In practice, the hair is optionally rewetted before application of the reducing composition.

When the operation is carried out starting from a reducing composition prepared at the time of use, the latter thickens on contact with the wet hair as the organic absorbing agent gradually swells with water. The composition thickens sufficiently rapidly not to flow onto the scalp. During this swelling, the reducing active principle gradually penetrates into each individual hair, less rapidly than a liquid reducing agent but over the whole of each individual hair, from the root to the end.

The thickened mixture deposited on the hair resembles an "icing." This "icing" makes it possible to reduce the smell of the thiols and reduced hairs. This makes it possible to allow the reducing composition to act without placing a cap over the hair during the leave-in time.

The hair treated with the reducing composition (a) is left to stand for a time sufficient for the reduction of the hair. This time is generally the order of 10 to 15 minutes.

According to another particularly advantageous aspect of the process of the invention, prior to the application of the neutralizing composition (b) of stage (ii) but after a certain leave-in time for the hair treated with the reducing composition (a), the hair is carefully rinsed, generally with water, until the reducing composition has been completely removed.

Another important stage of the process of the invention consists of the application of a neutralizing composition (b). This neutralizing composition (b) can comprise any oxidizing agent known per se.

The neutralizing composition (b) advantageously comprises at least one oxidizing agent chosen from hydrogen peroxide, urea hydrogen peroxide, alkali metal bromates, or persalts, such as perborates and persulphates.

The neutralizing composition (b) also comprises pH-regulating agents, so as to maintain an acidic pH.

The neutralizing composition (b) or the reducing composition (a) can preferably additionally comprise additives chosen from anionic, nonionic or amphoteric polymers, surfactants, silicones, waxes, thickeners, penetrating agents, fatty alcohols, lanolin derivatives, ceramides, active ingredients, agents for combating hair loss, antidandruff agents, suspending agents, sequestering agents, opacifying agents, stabilizing agents, colourants, silicone or non-silicone sunscreen agents, preservatives or fragrances.

With the aim in particular of improving the cosmetic properties of the hair, the neutralizing composition (b) or the reducing composition (a) can additionally comprise cationic polymers. The term "cationic polymers" is understood to mean any polymer comprising cationic groups or groups which can be ionized to cationic groups.

Mention may more particularly be made, as cationic polymers which can be used in the context of the invention, of polymers of the following types: polyamine, polyamidoamide, poly(quaternary ammonium), silicone cationic polymers, polyalkyleneimine, in particular polyethyleneimines, polymers comprising vinylpyridine or vinylpyridinium units, condensates of polyamine and of epichlorohydrin, poly(quaternary ureylene)s, cyclopolymers and chitin derivatives.

Preference is given, among all the cationic polymers capable of being used in the context of the present invention, to the use of cyclopolymers, in particular dimethyldiallylammonium chloride homopolymers, sold under the name Merquat® 100 by Merck, and certain di(quaternary ammonium) polymers, such as hexadimetrine chloride from Chimex.

According to the invention, use may also be made of cationic polymers in the latex or pseudolatex form, that is to say in the form of a dispersion of particles of insoluble polymers.

According to the invention, the cationic polymer or polymers can represent from 0.01% to 20% by weight, preferably from 0.1 to 15% by weight, of the total weight of the final composition.

In the final stage of the process according to the invention (stage (iii)), the hair thus treated is rinsed after a leave-in time necessary for the neutralization of the hair. This time is generally of the order of 5 minutes.

The mechanical means (rollers, curlers and similar devices) which kept the hair under tension in the desired shape throughout the treatment are removed from the hair, before or after rinsing out the neutralizing composition, it being possible for the elimination of the tensioning means optionally to be followed by the re-application of a certain amount of neutralizing composition (b).

Finally, hair exhibiting, for example, permanent uniform and beautiful curls can be obtained.

The process is completed by natural drying or by drying by any drying means (infrared, hair dryer and other devices), in order to obtain beautiful curling.

The invention may be better understood with the help of the example which follows and which constitutes an advantageous embodiment of the process in accordance with the invention.

EXAMPLE

The following compositions are prepared:
For the reducing composition, the reducing liquid part A, on the one hand, and the part B, on the other hand, are prepared.

Reducing Composition

| Liquid part A: | | |
|---|---|---|
| Aqueous ammonia (comprising 20.5% of ammonia) | | 12.1 g |
| Thioglycolic acid | | 9.4 g |
| Oxyethylenated oleyl alcohol (20 mol of ethylene oxide) | | 1.1 g |
| Fragrance | | 0.5 g |
| Diethylenetriaminepentaacetic acid, pentasodium salt, as a 40% aqueous solution | | 0.4 g |
| Demineralized water | q.s. | 90 g |
| Powder part B: | | |
| Primojel (supplier Avebe, potato carboxymethylstarch, sodium salt, weakly crosslinked) | | 10 g |

Neutralizing composition

| Hydrogen peroxide as a 50% solution | | 4.8 g |
|---|---|---|
| Lauryldimethylamine oxide in aqueous solution (30%) | | 2.15 g |
| p-Ethoxyacetanilide | | 0.05 g |
| Fragrance | | 0.2 g |
| Citric acid | | 0.1 g |
| 8-Hydroxyquinoline sulphate | | 0.0125 g |
| Demineralized water | q.s. | 100 g |

At the time of use, the reducing liquid A and the powder B are mixed while vigorously stirring. The mixture is left to stand for 1 minute.

The fluid suspension obtained is again stirred before application to wet hair.

The reducing composition thickens on contact with the wet hair, wound beforehand around curlers.

The composition is left on the hair for 15 minutes.

The hair is subsequently rinsed.

The neutralizing composition is subsequently applied to all the curlers. A leave-in time of 5 minutes is observed before rinsing the hair.

The curled hairstyle obtained exhibits uniform curls. During application, emanations of an unpleasant smell are greatly reduced, as is irritation of the scalp.

The invention claimed is:

1. A process for the permanent deformation and/or shaping of a keratinous substance, comprising:
   (i) applying to the keratinous substance a reducing composition (a) combining at least one reducing agent and at least one organic absorbing agent which is a crosslinked sodium carboxymethylcellulose, a modified starch, or mixtures thereof;
   (ii) placing the keratinous substance under mechanical tension before, during or after the application of step (i);
   (iii) applying a neutralizing composition (b) after a leave-in time necessary for reduction of the keratinous substance; and
   (iv) rinsing the keratinous substance after a leave-in time necessary for neutralization of the keratinous substance;
   wherein the reducing composition (a) is a ready-to-use reducing composition obtained by mixing, at the time of use, a reducing liquid comprising at least one reducing agent and an organic absorbing agent, the concentration of organic absorbing agent in the reducing composition (a) being between 7 and 11% by weight with respect to the total weight of the composition.

2. The process of claim 1, wherein the keratinous substance is hair.

3. The process of claim 1, wherein the organic absorbing agent has a static water absorption capacity of greater than or equal to five times the weight of the organic absorbing agent.

4. The process of claim 1, wherein the organic absorbing agent has a static water absorption capacity of greater than or equal to ten times the weight of the organic absorbing agent.

5. The process of claim 1, wherein the organic absorbing agent is a carboxymethylstarch.

6. The process of claim 1, wherein the ready-to-use reducing composition is left to stand for at least 1 minute after the mixing.

7. The process of claim 1, wherein the organic absorbing agent is in suspension in a hydrophobic oil.

8. The process of claim 1, wherein the reducing composition (a) is applied to wet hair.

9. The process of claim 1, wherein the hair is rinsed prior to the application of the neutralizing composition (b).

10. The process of claim 1, wherein the at least one reducing agent is thioglycolic acid, thiolactic acid, cysteine, cysteamine or glycerol thioglycolate.

11. The process of claim 1, wherein the neutralizing composition (b) comprises hydrogen peroxide, urea hydrogen peroxide, an alkali metal bromate, or a persalt.

12. The process of claim 11, wherein the persalt is a perborate or persulfate.

13. The process of claim 1, wherein the reducing composition (a) additionally comprises ammonia, monoethanolamine, diethanolamine, triethanolamine, isopropanolamine, 1,3-propanediamine, an alkali metal or alkaline earth metal or ammonium carbonate or bicarbonate, an organic carbonate, or an alkali metal or alkaline earth metal hydroxide or mixtures thereof.

14. The process of claim 1, wherein the reducing composition (a), the neutralizing composition (b) or both the reducing composition (a) and the neutralizing composition (b) additionally comprises a surfactant, a cationic, anionic, nonionic or amphoteric polymer, a silicone, a wax, a thickener, a penetrating agent, a fatty alcohol, a lanolin derivative, a ceramide, an active ingredient, an agent for combating hair loss, an antidandruff agent, a suspending agent, a sequestering agent, an opacifying agent, a stabilizing agent, a colorant, a silicone or nonsilicone sunscreen agent, a preservative or a fragrance.

* * * * *